United States Patent [19]

Taszarek et al.

[11] 4,380,929

[45] Apr. 26, 1983

[54] METHOD AND APPARATUS FOR ULTRASONIC DETECTION OF NEAR-SURFACE DISCONTINUITIES

[75] Inventors: Bruce J. Taszarek, Mt. Lebanon; Warren R. Junker, Monroeville, both of Pa.

[73] Assignee: Westinghouse Electric Corp., Pittsburgh, Pa.

[21] Appl. No.: 279,504

[22] Filed: Jun. 30, 1981

[51] Int. Cl.³ .......................................... G01N 29/04
[52] U.S. Cl. .......................................... 73/579; 73/602
[58] Field of Search ................................... 73/579, 602

[56] References Cited

U.S. PATENT DOCUMENTS 3,662,289  5/1972  Adler et al. ............................ 73/602
3,776,026 12/1973  Adler et al. ............................ 73/602
3,996,791 12/1976  Niklas et al. ........................... 73/602
4,052,889 10/1977  Mucciaroi .............................. 73/602

*Primary Examiner*—Anthony V. Ciarlante
*Attorney, Agent, or Firm*—D. Schron

[57] ABSTRACT

Near-surface discontinuities, or flaws, within a workpiece are determined by transmitting acoustic energy into the workpiece. If a discontinuity is present the acoustic energy will resonate in the section of the material between the discontinuity and the surface. Acoustic energy emerging from the section as a result of the resonating is detected and analyzed to determine this fundamental frequency, from which the half wavelength and depth of the discontinuity may be determined. The procedure is also applicable for determining the thickness of relatively thin sheets of material.

9 Claims, 5 Drawing Figures

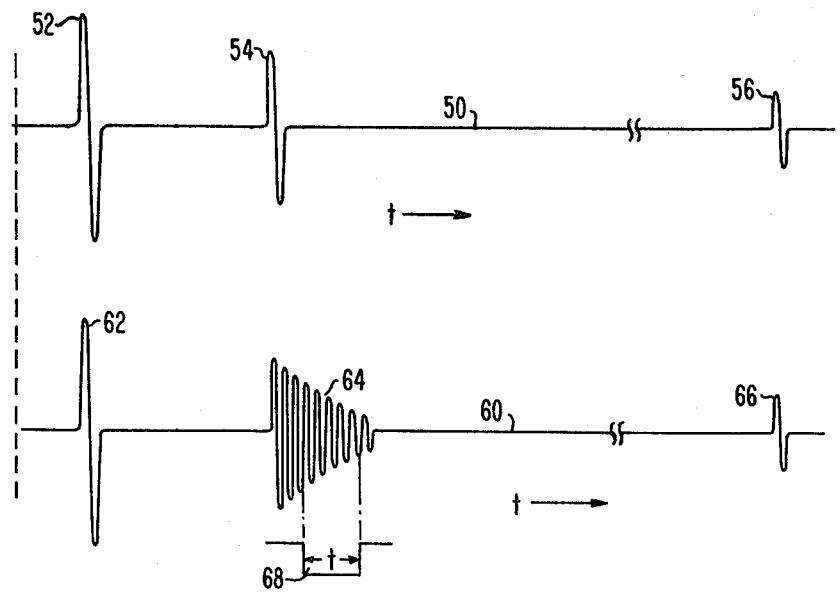
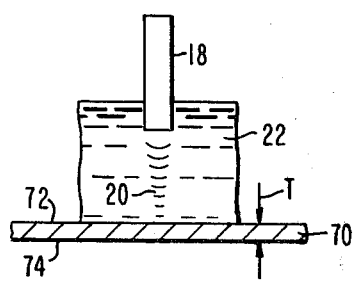
FIG. 4
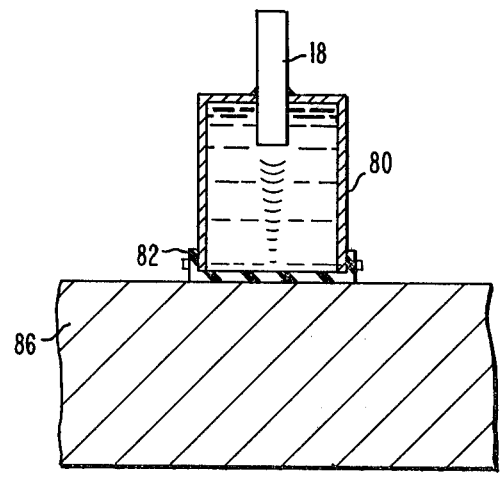
FIG. 5

METHOD AND APPARATUS FOR ULTRASONIC DETECTION OF NEAR-SURFACE DISCONTINUITIES

BACKGROUND OF THE INVENTION

1. Field of the Invention

The invention in general relates to the ultrasonic testing of materials, and particularly for the detection of discontinuities extremely close to the surface of the material being tested.

2. Description of the Prior Art

Various ultrasonic techinques are widely used for the detection of flaws in materials such as metal stock or finished parts. Basically, an ultrasonic transducer projects a pulse of acoustic energy into the workpiece under test and any discontinuity or flaw within the workpiece will reflect the projected acoustic pulse. This reflected pulse may then be detected by the same or a separate transducer to thereby give an indication of the presence and depth of the discontinuity.

In some systems a plurality of transducers are utilized for projection and reception of acoustic pulses together with computer analysis of the reflected wave forms so as to obtain more information regarding not only the depth but the size and orientation of the discontinuity.

With these systems, the limits on resolution with, for example steel-based alloys, generally approach approximately 50 mils (1.27 mm). That is, these systems are not able to detect flaws within a few mils of the surface.

A need, therefore, exists for an arrangement which can detect these near-surface flaws and the present invention is operable for detecting some of these flaws.

SUMMARY OF THE INVENTION

The present invention is operable to determine near-surface discontinuities in a workpiece by positioning an ultrasonic projector above an area of the workpiece to be tested and thereafter energizing the projector so as to project a pulse of acoustic energy toward the area. Energy reflected from the area is received and if there are any near-surface discontinuities, the acoustic energy entering the material will resonate in the section between the surface and the discontinuity and will emerge on successive reflections so as to be picked up by an ultrasonic receiver, the output signal of which will contain a fundamental frequency component related to the half-wavelength resonance of the section. The reflected signal is examined for this frequency component and if present, an analysis is made so as to allow the computation of the depth of the discontinuity from the surface of the material. The analysis preferably includes a Fast Fourier Transform for obtaining the fundamental frequency component.

BRIEF DESCRIPTION OF THE DRAWINGS

FIG. 3 illustrates waveforms present during the operation of the apparatus of FIG. 1;

FIG. 4 illustrates another use for the apparatus for determining the thickness of sheet material; and FIG. 5 illustrates an alternate coupling arrangement for acoustic energy.

DESCRIPTION OF THE PREFERRED EMBODIMENT

Figure 1:
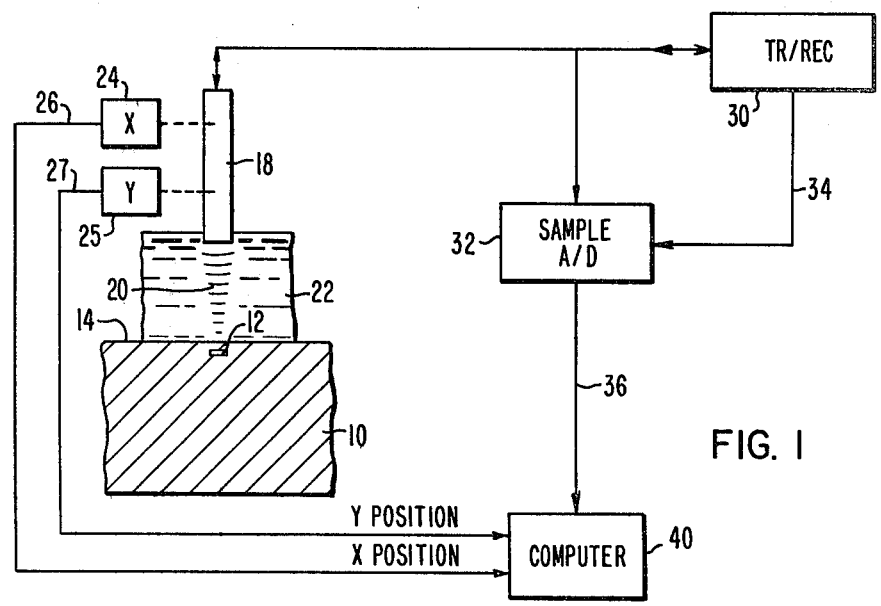
FIG. 1 is a block diagram illustrating one embodiment of the present invention.

Referring now to FIG. 1, there is illustrated in cross section, a workpiece 10 having a flaw 12 therein extremely near the surface 14. Flaw 12 can be considered as a discontinuity in the material of the workpiece and by way of example may be a crack, or a material other than that of the workpiece, or in general, anything having a different acoustic impedance than the workpiece itself.

The surface of the workpiece is subject to acoustic impingement with the provision of a transducer 18 operable to periodically project acoustic pulses through a coupling medium 22 toward the surface 14.

Transducer 18 is scanned in two dimensions over the surface 14 by means of X and Y drivers 24 and 25, each being additionally operable to provide respective signals on lines 26 and 27 indicative of the X and Y coordinates of the transducer 18.

Transducer 18 will convert pulses of electrical energy into corresponding pulses of acoustic energy and will convert reflected acoustic pulses into an electrical signal. The transmit/receive unit 30 is operable to supply the electric pulses for transducer energization and is additionally operable to receive and detect the electrical signals provided by the transducer. The return signals are also provided to an analog-to-digital converter 32 which in one mode of operation will convert the analog return signal into a digital equivalent when provided with an enabling signal on line 34 from the transmit/receive unit 30. This enabling signal will be provided when the return signal from transducer 18 includes a component other than the acoustic return surface 14, as will be explained.

Figure 2:
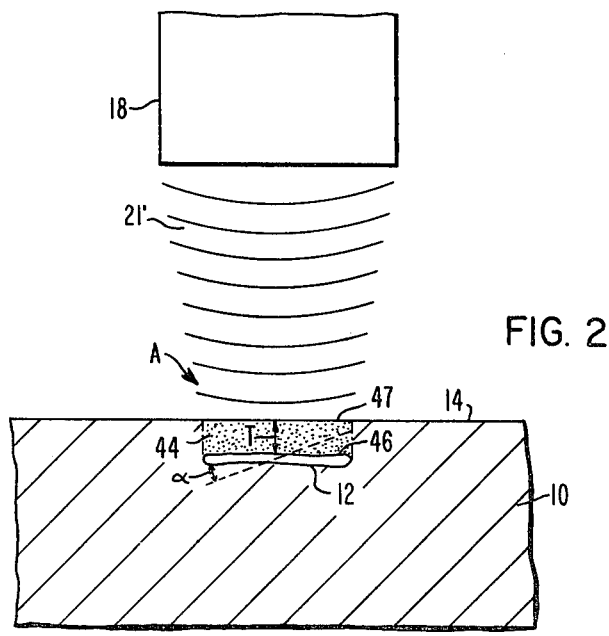
FIG. 2 illustrates a cross-sectional view of a test piece which includes a near-surface discontinuity.

The digital representation of the sampled signal is provided on line 36 to computer 40 which in a preferred embodiment processes the information by means of the well-known Fast Fourier Transform to determine the fundamental frequency included in the return signal, from which the depth of the flaw may be determined. The position of the flaw is also determined by means of the position signals on lines 26 and 27 provided by the X and Y drivers 24 and 25. The principle of operation may be better understood with reference to FIG. 2 which is an enlargement of the flaw region shown in FIG. 1.

In a preferred embodiment, transducer 18 is of the type which will focus acoustic energy onto the surface 14 of workpiece 10 so as to concentrate maximum energy. Thus, in FIG. 2 an acoustic pulse 21' is illustrated and will impinge upon the general area A below which is the flaw, or discontinuity 12. The thickness of the material above the flaw, that is, between the discontinuity and surface, is designated T. After the acoustic pulse 21' impinges upon surface 14 it enters the material above the flaw 12 (shown stippled) and will resonate therein at a certain fundamental frequency dependent upon the thickness (or depth) T. The acoustic energy successively reflects off of the rear surface 46 and front surface 47 (both of which are acoustic impedance mismatches with their respective adjacent environments). During this reverberation some acoustic energy passes out through the front surface 47 of the section 44 and is detected by the same transducer 18 which will provide an electrical equivalent output signal to the computer via the A to D converter. This electrical signal is analyzed for its frequency components to derive a fundamental frequency from which the wavelength of acoustic energy resonating in the material may be determined. Knowing the wavelength of acoustic energy in the material, the thickness of the section and, accordingly, the depth to flaw 12 may be obtained.

Basically, the determination can be made utilizing the basic relationship:

$$c = f\lambda \quad (1)$$

where c is the speed of sound in the material, f is frequency and λ is the wavelength of the sound in the material. For a particular material the speed of sound c will be known and the computer will determine the fundamental frequecy f so that λ may be determined from the relationship:

$$\lambda = c/f \quad (2)$$

The distance from the front surface 47 to the rear surface 46 of section 44 is equivalent to a half wavelength so that:

$$\lambda/2 = c/2f = T \quad (3)$$

The above analysis for determining thickness T assumes a relatively uniform thickness of section 44. If the flaw 12 is not parallel to surface 14 and is within the limits defined by the angle α, a resonant frequency will still be provided so that an average value of T may be calculated or the mere presence of a flaw may be established.

In summary, therefore, an acoustic pulse entering a section 44 will resonate therein at some fundamental frequency related to the distance from the front surface to the rear surface of the section and which distance is equivalent to a half wavelength. The acoustic signal emerging from the section during alternate reflections includes a fundamental frequency component which may be determined by receiving the emerging signal, converting it into an equivalent electrical signal, and providing it to a computer where a Fast Fourier Transform analysis may be performed to determine the fundamental frequency from which the half wavelength or thickness of the resonating section and, accordingly, the depth of the discontinuity may be established.

FIG. 3 serves to illustrate the various wave forms which may exist throughout the system of FIG. 1. In wave form 50, representing the absence of a sub-surface discontinuity, pulse 52 is indicative of the initial acoustical pulse provided by transducer 18. Depending upon the distance of transducer from the workpiece 10, the initial acoustic pulse will be reflected from the surface 14 and pulse 54 of waveform 50 represents this surface-reflected pulse. Acoustic energy will additionally enter the workpiece 10 and will be reflected from the rear surface thereof and this condition is represented by pulse 56. The distance between pulses 54 and 56, therefore, is indicative of the total thickness of the workpiece 10.

Curve 60 represents the waveform when a near-surface defect is present. Pulse 62 represents the transmitted pulse while the damped oscillation 64 represents the return with a near-surface defect present and pulse 66 is that due to the rear surface reflection.

The receiver portion of the transmit/receive unit 30 is operable when oscillation 64 is present to provide a gating pulse 68 to enable the A to D converter 32 to sample the osciallatory signal for a time period t. This sampling period is sufficiently long so as to enable the Fast Fourier Transform to be performed. During the scanning process one or more defects may be detected and the computer will provide an output indicating the presence of a defect, its average distance from the surface and its precise location on an XY coordinate system.

Gate 68 can enable the A to D converter 32 (FIG. 1) to sample the entire oscillatory signal including the interface signal. If the original interface signal 54 has been previosuly stored, this can be subtracted from signal 64 to isolate the reflection from the near surface flaw. Numerous varieties of digital filtering and comparison techniques can be implemented to improve resolution capabilities.

The apparatus and the technique described herein is not only useful for detecting discontinuities as close as 3 to 5 mils from the surface, but is also applicable for detecting the thickness of extremely thin sheet material such as illustrated in FIG. 4. In FIG. 4 the transducer 18 is arranged to project acoustic pulses 20 through the coupling medium 22 to a relatively thin sheet of material 70 having a nominal thickness T between its front and rear surfaces 72 and 74, respectively. Although not illustrated in FIG. 4, the apparatus of FIG. 1 is utilized in an identical manner so as to set up a half wavelength plate resonance mode of vibration in the vicinity of acoustic impingement whereupon the signals provided by the resonating area will be digitized and analyzed by the Fast Fourier Transform process to yield a frequency and, accordingly, a thickness value. With the arrangement of FIG. 4 the discontinuity is, in effect, the rear surface-ambient medium interface. The sheet thickness and thickness consistency may then be obtained by scanning in any predetermined pattern.

In many instances a piece to be tested for flaws, as in the case of FIG. 1, or for thickness, as in the case of FIG. 4, may be immersed in a tank of water with the water thereby constituting the coupling medium 22. An alternative arrangement is illustrated in FIG. 5 and includes a fluid-filled container 80 into which is placed transducer 18 at one end thereof and which includes an acoustic window such as neoprene rubber 82 secured to the lower open end of container 80 and in direct contact with a workpiece 86 under test.

Although the arrangement described herein utilizes scanning means for moving the transducer of the piece to be tested, it is understood that other arrangements that do not involve the automatic scanning may be utilized. For example, the transducer may be placed over different areas manually and the analysis of the signal therefrom need not be made by a computer utilizing the Fast Fourier Transform analysis. The determination of the fundamental frequency of the return signal may be accomplished with an analog spectrum analyzer with the depth or thickness determination being calculated by a user. Although this latter method would require a significant amount of time (for example 10 and 20 seconds per analysis) satisfactory results are obtainable. Use of the computer, however, not only allows for a quicker determination relative to a large scanned area but also affords the user software subroutines which may incorporate any desired filtering algorithms to improve the signal-to-noise ratio of the wave form or its transform, thus providing a further advantage over the analog technique.

We claim:

1. A method of determining near-surface discontinuities in a workpiece comprising the steps of:

(A) positioning an ultransonic projector above an area of said workpiece;
(B) energizing said projector to project a pulse of acoustic energy toward said area;
(C) receiving acoustic energy reflected as a result of said projection;
(D) determining, from said received acoustic energy, the fundamental frequency of acoustic energy resonating in a section of workpiece material between a near-surface discontinuity and the surface of said workpiece;
(E) determining from said frequency the average thickness of said section, and therefore the average depth of said discontinuity.

2. A method according to claim 1 which includes the step of:
(A) scanning said projector over the surface of said workpiece.

3. A method according to claim 2 which includes:
(A) recording the scanning position of said projector.

4. A method according to claim 1 wherein:
(A) said acoustic energy is projected through a coupling liquid.

5. A method according to claim 1 wherein:
(A) said projected acoustic energy is focussed to a relatively small area.

6. A method according to claim 1 which includes:
(A) determining said fundamental frequency of vibration by means of a Fast Fourier Transform analysis.

7. A method according to claim 6 wherein:
(A) said analysis is performed only if said reflected acoustic energy contains more than just a surface reflection content.

8. A method according to claim 1 wherein:
(A) said projector also is the receiver transducer for reflected acoustic energy.

9. A method according to claim 1 wherein:
(A) said workpiece is a thin sheet of material and said discontinuity is the rear surface-ambient medium interface.

* * * * *